(12) United States Patent
Hosoi et al.

(10) Patent No.: US 10,617,710 B2
(45) Date of Patent: Apr. 14, 2020

(54) AGENT FOR SEDATING RESPONSE TO EXTERNAL STIMULATION IN SKIN AND METHOD FOR SEDATING THAT RESPONSE

(71) Applicant: Shiseido Company, Ltd, Chuo-ku, Tokyo (JP)

(72) Inventors: Junichi Hosoi, Yokohama (JP); Kaori Inoue, Yokohama (JP); Shoko Yamada, Yokohama (JP); Minako Sato, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 590 days.

(21) Appl. No.: 15/124,767

(22) PCT Filed: Mar. 12, 2014

(86) PCT No.: PCT/JP2014/057629
§ 371 (c)(1),
(2) Date: Sep. 9, 2016

(87) PCT Pub. No.: WO2015/136718
PCT Pub. Date: Sep. 17, 2015

(65) Prior Publication Data
US 2017/0014444 A1    Jan. 19, 2017

(51) Int. Cl.
| A61K 36/73  | (2006.01) |
| A61K 36/064 | (2006.01) |
| A61K 31/716 | (2006.01) |
| A61K 31/77  | (2006.01) |
| A61K 36/738 | (2006.01) |

(52) U.S. Cl.
CPC ............ *A61K 31/716* (2013.01); *A61K 31/77* (2013.01); *A61K 36/738* (2013.01)

(58) Field of Classification Search
CPC .............................. A61K 36/73; A61K 36/064
USPC ............................................. 424/195.15, 765
See application file for complete search history.

(56) References Cited

U.S. PATENT DOCUMENTS

| 5,968,530 A * | 10/1999 | Arquette | A61K 8/19 424/401 |
| 6,352,698 B1 | 3/2002 | Castelli et al. | |
| 2003/0180335 A1 | 9/2003 | Ohmori et al. | |
| 2005/0129618 A1 | 6/2005 | Ashida et al. | |
| 2013/0142775 A1 | 6/2013 | Chen et al. | |

FOREIGN PATENT DOCUMENTS

| JP | 2000-236775 A | 9/2000 |
| JP | 2000-239144 A | 9/2000 |
| JP | 2001-502685 A | 2/2001 |
| JP | 2003-277221 A | 3/2002 |
| JP | 2003-194809 A | 7/2003 |
| JP | 2004-083541 A | 3/2004 |
| JP | 2004-339113 A | 12/2004 |
| JP | 2013-516991 A | 5/2013 |
| JP | 2014-080386 A | 5/2014 |
| WO | WO 98/17246 A1 | 4/1998 |
| WO | WO 2011/088244 A1 | 7/2011 |

OTHER PUBLICATIONS

Ohmori et al. "Development of Novel Multifunctional Cosmetic Raw Materials and Their Applications. I. Characterization of a Random Copolymer of Polyoxyethylene/Polyoxypropylene Dimethyl Ether", J. Oleo Sci., vol. 55, No. 7, 365-375 (2006). (Year: 2006).*
Zulli et al, "Anti-Aging and Photoprotecting Effects of Carboxymethyl-ated Glucan from Baker's Yeast", Personal Care Ingredients Asia China: p. 178-183. (1999). (Year: 1999).*
Holzer et al,. "Role of Extracellular Adenosine Triphosphate in Human Skin," Journal of Cutaneous Medicine and Surgery, Apr. 2004, 8(2):90-96.
Kawamura et al., "Severe dermatitis with loss of epidermal Langerhans cells in human and mouse zinc deficiency," The Journal of Clinical Investigation, Feb. 2012, 122(2):722-732.
Koivukangas et al., "Suction Blister Model of Wound Healing," from: Methods in Molecular Medicine, 2003, 78:255-261.
Mizumoto et al., "CD39 is the dominant Langerhans cell-associated ecto-NTPDase: Modulatory roles in inflammation and immune responsiveness," Nature Medicine, Apr. 2002, 8(4):358-365.
Yagi et al., "Polyoxyethylene/polyoxypropylen dimethyl ether (EPDME) improves the structure of intercellular lipids in SDS-induced dry skin," J. Cosmet. Sci., Jan./Feb. 2010, 61:39-48.

* cited by examiner

*Primary Examiner* — Michael Barker
*Assistant Examiner* — Deborah A Davis
(74) *Attorney, Agent, or Firm* — Foley & Lardner LLP

(57) ABSTRACT

An object of the present invention is to provide an agent for sedating the response of skin to external stimulation. The aforementioned object was achieved by finding a component that promotes CD39 gene expression in Langerhans cells. More specifically, the present invention is based on the finding that the combination of carboxymethyl-beta glucan or a salt thereof polyoxyethylene (POE)/polyoxypropylene (POP) random copolymer dimethyl ether and rosewater promotes CD39 gene expression.

3 Claims, 1 Drawing Sheet
Specification includes a Sequence Listing.

AGENT FOR SEDATING RESPONSE TO EXTERNAL STIMULATION IN SKIN AND METHOD FOR SEDATING THAT RESPONSE

SEQUENCE LISTING

The instant application contains a Sequence Listing which has been filed electronically in ASCII format and is hereby incorporated by reference in its entirety. Said ASCII copy, created on Oct. 31, 2019, is named 053466-0593_SL.txt and is 1,244 bytes in size.

TECHNICAL FIELD

The present invention relates to a pharmaceutical agent that reduces the response of the skin to external stimulation.

BACKGROUND ART

The skin is an organ located on the outermost layer of the body, and is continuously exposed to stimulation from the outside such as ultraviolet rays, physical stimulation, chemical stimulation or biological invasion.

The skin has a three-layer structure consisting of the epidermis, dermis and subcutaneous tissue, and among these, the epidermis of the outermost layer is composed of keratinocytes, Langerhans cells and melanocytes and the like, and functions to prevent water loss and entry of foreign bodies and to protect the body from ultraviolet rays and other elements of the external environment. Upon receiving external stimulation, keratinocytes release a stimulation response factor, and then surrounding keratinocytes which receive the signal of the released stimulation reaction factor secrete inflammatory cytokines, which result in induction of immune cells, and the occurrence of inflammation at the stimulated site (Non-Patent Document 1). In addition, it has been determined from recent research that Langerhans cells fulfill an important role in the immune function of skin through antigen processing and their antigen presenting ability. Langerhans cells promptly make contact with and process antigens entering from the outside as foreign bodies, transport them to lymph nodes and present them to T cells followed by induction of a series of immune response reactions. As a result, Langerhans cells have been determined to contribute to functions that counter chemical stimulation and biological invasion. On the other hand, Langerhans cells express CD39, which functions as an ATPase, and as a result thereof, has the ability to lower the amount of ATP, an extracellular stimulation response factor (Non-Patent Document 2). Extracellular ATP is recognized to be one of the signals of the inflammatory process. Thus, Langerhans cells are thought to reduce skin disorders caused by ultraviolet rays or physical stimulation by contributing to the reduction of inflammation by mediating the degradation of extracellular ATP. It has been reported that, when the number of Langerhans cells decreases due to zinc deficiency, the function of CD39 molecules of sedating the response of skin to external stimulation decreases, thereby resulting in an excessive response to stimulation that causes excessive inflammation (Non-Patent Document 3).

Thus, since enhancement of skin immune function, decreased inflammation and reduction of sunburn and other skin disorders can be expected to be realized by increasing or activating Langerhans cells, screening methods using Langerhans cells as an indicator (Patent Document 1) and pharmaceutical reagents or reduction inhibitors that increase or activate Langerhans cells (Patent Document 2) are being developed.

PRIOR ART DOCUMENTS

Patent Documents

[Patent Document 1] Japanese Unexamined Patent Publication No. 2000-236775
[Patent Document 2] Japanese Unexamined Patent Publication No. 2000-239144
[Patent Document 3] Japanese Unexamined Patent Publication No. 2004-83541

Non-Patent Documents

[Non-Patent Document 1] Holzer, A. M. and Granstein, R. D., "Role of extracellular adenosine triphosphate in human skin", J. Cutan. Med. Surg., 2004, 8(2): 90-96
[Non-Patent Document 2] Mizumonot, N., et al., "CD 39 is the dominant Langerhans cell-associated ectoTNPDase: Modulatory roles in inflammation and immune responsiveness", Nat. Med., 2002, 8(4): 358-365
[Non-Patent Document 3] Kawamura, T., et al., "Severe dermatitis with loss of epidermal Langerhans cells in human and mouse zinc deficiency", J. Clin. Invest., 2012, 122(2): 722-732
[Non-Patent Document 4] Koivukangas, V. and Oikarinen, A.: Suction Blister Model of Wound Healing (2003), Methods in Molecular Medicine, 78: 255-261

DISCLOSURE OF THE INVENTION

Problems to be Solved by the Invention

An object of the present invention is to develop a pharmaceutical agent or method for sedating the response of the skin to external stimulation by mediating activation of Langerhans cells.

Means for Solving the Problems

As a result of conducting extensive studies on indicators of activation of Langerhans cells, the inventors of the present invention found that CD39 gene expression can be used as an indicator thereof. When screening was carried out using CD39 gene expression as an indicator, polyoxyethylene (POE)/polyoxypropylene (POP) random copolymer dimethyl ether, sodium carboxymethyl-beta glucan and rosewater were respectively found to be able to increase depressed CD39 gene expression in Langerhans cells under stress conditions. Moreover, it was surprisingly found that, in the case of using polyoxyethylene (POE)/polyoxypropylene (POP) random copolymer dimethyl ether, sodium carboxymethyl-beta glucan and rosewater in combination, CD39 gene expression in Langerhans cells increases synergistically, thereby leading to the present invention as described below.

Thus, the present invention relates to that described below.

(1) A CD39 gene expression promoter, comprising three components consisting of carboxymethyl-beta glucan or a salt thereof, polyoxyethylene (POE)/polyoxypropylene (POP) random copolymer dimethyl ether and rosewater.

(2) A use of three components consisting of carboxymethyl-beta glucan or a salt thereof, polyoxyethylene (POE)/ polyoxypropylene (POP) random copolymer dimethyl ether and rosewater to produce a CD39 gene expression promoter.

(3) A method for promoting CD39 gene expression, comprising administering a composition comprising three components consisting of carboxymethyl-beta glucan or a salt thereof, polyoxyethylene (POE)/polyoxypropylene (POP) random copolymer dimethyl ether and rosewater to a subject requiring promotion of CD39 gene expression.

(4) An agent for sedating response to external stimulation in skin, comprising three components consisting of carboxymethyl-beta glucan or a salt thereof, polyoxyethylene (POE)/polyoxypropylene (POP) random copolymer dimethyl ether and rosewater.

(5) A use of three components consisting of carboxymethyl-beta glucan or a salt thereof, polyoxyethylene (POE)/polyoxypropylene (POP) random copolymer dimethyl ether and rosewater for producing an agent for sedating response to external stimulation in skin.

(6) A method for sedating the response of skin to external stimulation, comprising administering a composition comprising three components consisting of carboxymethyl-beta glucan or a salt thereof, polyoxyethylene (POE)/polyoxypropylene (POP) random copolymer dimethyl ether and rosewater to a subject requiring reduction of the response of skin to external stimulation.

(7). An agent for sedating skin immune response, comprising three components consisting of carboxymethyl-beta glucan or a salt thereof, polyoxyethylene (POE)/polyoxypropylene (POP) random copolymer dimethyl ether and rosewater.

(8) A use of three components consisting of carboxymethyl-beta glucan or a salt thereof, polyoxyethylene (POE)./polyoxypropylene (POP) random copolymer dimethyl ether and rosewater for producing an agent for sedating skin immune response.

(9) A method for sedating skin immune response, comprising administering a composition comprising three components consisting of carboxymethylybeta glucan or a salt thereof, polyoxyethylene (POE)/polyoxypropylene (POP) random copolymer dimethyl ether and rosewater to a subject requiring reduction of skin immune response.

Effects of the Invention

The present invention is able to demonstrate at least one of the effects of increasing CD39 gene expression, sedating the response of the skin to external stimulation, and sedating skin immune response.

BEST MODE FOR CARRYING OUT THE INVENTION

Figure 1:
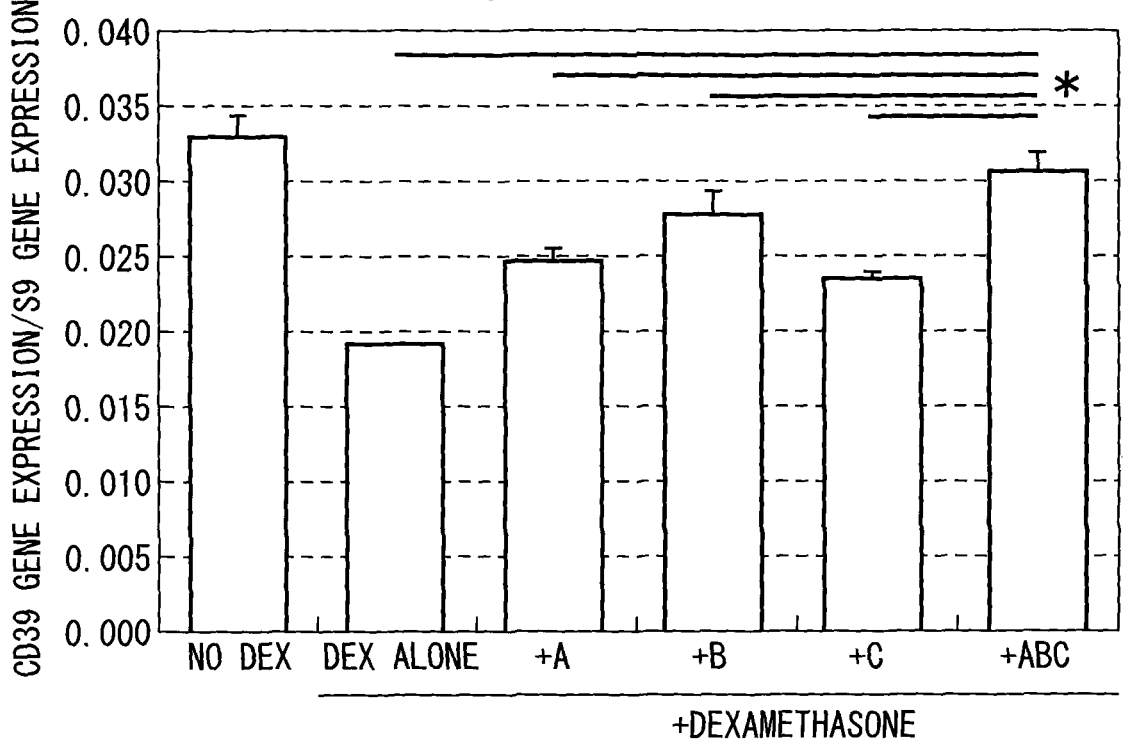
FIG. 1 indicates that CD39 gene expression, which had been depressed by addition of a stress hormone in the form of dexamethasone, is significantly restored in Langerhans cells by the simultaneous addition of three components (A, B, C) consisting of polyoxyethylene (POE) 14/polyoxypropylene (POP) 7 random copolymer dimethyl ether (A), sodium carboxymethyl-beta glucan (B) and rosewater (C).

The present invention relates to a CD39 gene expression promoter, an agent for sedating response to external stimulation in skin, and an agent for sedating skin immune response, comprising three components consisting of β-glucan, polyoxyethylene (POE) 14/polyoxypropylene (POP) 7 random copolymer dimethyl ether and rosewater.

CD39, of which expression thereof is promoted by a CD39 gene expression promoter, indicates a protein referred to as ectonucleoside triphosphate diphosphohydrolase-1 (ENTPD1), and is an enzyme that respectively hydrolyzes ATP/UTP and ADP/UDP to AMP and other nucleosides. CD39 is a membrane protein having two membrane-permeating domains, and is recognized to be expressed in Langerhans cells as well as other cells including T cell subsets, B cells and dendritic cells. CD39 has the action of degrading extracellular ATP, and as a result of this action, cells that express CD39 have been determined to have a role of sedating inflammation.

Although ATP is used as an energy medium within cells after having been degraded by the enzyme activity of CD39, outside cells, it is a substance that fulfills the role of an information transmitter. For example, ATP is known to act as a neurotransmitter in the nervous system. On the other hand, in the skin, ATP is released outside cells either in response to mechanical stimulation, chemical stimulation or ultraviolet stimulation, or as a result of cell destruction, and is thought to contribute to immunity, allergies and inflammatory reactions by inducing immune cells through the promotion of the production of cytokines and chemokines by acting on nearby immune cells (Non-Patent Document 1). Thus, cells that express CD39 are able to reduce an excessive response by the skin, and particularly the epidermis, to external stimulation, or reduce excessive immune response, by degrading extracellular ATP.

In the skin, cells that express CD39 consist mainly of Langerhans cells and melanocytes, and promotion of gene expression of CD39 in the skin may be correlated with activation, proliferation, induction or inhibition of reduction of these cells, and particularly Langerhans cells. Langerhans cells are dendritic cells derived from bone marrow, they are migrating cells present from the prickle cell layer to the upper layer, and they express markers such as CD1a in addition to CD39. Examples of the functions of Langerhans cells include capturing and recognition of foreign bodies that have entered from the outside and presenting those foreign bodies to T cells, recognition of cancer cells, induction of immunotolerance and degradation of extracellular ATP, and Langerhans cells are mainly involved in immune response reactions in skin. Among the many functions of Langerhans cells, the action of degrading extracellular ATP mediated by CD39 makes it possible to reduce an excessive response to external stimulation as well as reduce an excessive immune response in the skin, and particularly in the epidermis. The CD39 gene expression promoter of the present invention refers to a pharmaceutical agent that promotes CD39 gene expression in cells expressing CD39, and particularly Langerhans cells.

Thus, the CD39 gene expression promoter of the present invention can also be used as an agent for sedating response to external stimulation. The agent for sedating response to external stimulation of the present invention reduces a response in the skin, and particularly in the epidermis, generated by external stimulation. Examples of external stimuli of skin include ultraviolet rays, mechanical stimulation, heat stimulation, cold stimulation, chemical stimulation and biological invasion. When the skin is subjected to these external stimuli, keratinocytes of the epidermis release stimulation response factors, and particularly ATP, outside the cells, and as previously explained, the extracellular ATP acts as an information transmitter resulting in the induction of immunity, allergies or an inflammatory reaction. Examples of mechanical stimulation include scratching, scraping and insect bites that lead to the occurrence of, for example, scratches, lacerations, wounds, redness or swelling, while sunburn or burns and the like result from stimulation by ultraviolet rays. Chemical stimulation is induced by a chemical substance exhibiting irritability with respect to the skin, is induced by, for example, acid, base or organic solvents, and results in the occurrence of eczema, rash or dermatitis. An example of biological invasion is bacterial infection.

The agent for sedating response to external stimulation in skin of the present invention is able to alleviate or reduce responses to these external stimuli in the skin, and particularly the epidermis, such as inflammation, or itching, redness, pain, burning sensation or swelling and the like caused by inflammation, making it possible to alleviate, reduce or treat symptoms exhibited as a result thereof. Thus, the agent for sedating response to external stimulation in skin of the present invention may be an agent for alleviating, treating or preventing the aforementioned symptoms. In addition, since immune response in skin can be reduced as a result of sedating response to external stimulation, the agent for sedating response to external stimulation in skin of the present invention may also be an agent for sedating skin immune response.

On the other hand, the agent for sedating response to external stimulation in skin of the present invention does not directly inhibit the cascade of the skin's stimulation response, but rather is thought to indirectly alleviate the stimulation response through promotion of gene expression of CD39 having the function of ATPase. Thus, the agent for sedating response to external stimulation enhances the ordinarily possessed function of skin of sedating an excessive response to external stimulation, thereby enabling it to function as an agent that enhances the function of sedating response to stimulation. As a result of using an agent that enhances the function of sedating response to stimulation on a regular basis even when inflammation is not present instead of administering directly to a site where inflammation is occurring, the function can be demonstrated of inhibiting an inflammatory response at the time of external stimulation in the form of, for example, itching, redness, pain, burning sensation, swelling or rash. Thus, although the agent that reduces response to external stimulation may be incorporated in a pharmaceutical, it is preferably incorporated in cosmetics, which are intended to be used on a regular basis. In the case the agent for sedating response to external stimulation in skin of the present invention is incorporated in a pharmaceutical, incorporating together with another pharmaceutical agent having an anti-inflammatory action makes it possible to assist or enhance the anti-inflammatory action of that pharmaceutical agent.

The agent for sedating response to external stimulation in skin of the present invention is also a pharmaceutical agent that reduces immune response in skin, and is able to contribute to the reduction of an immune response caused by a decrease in Langerhans cells in particular or an increase in extracellular ATP, and particularly to the reduction of excessive inflammation. Examples of excessive inflammation include chronic dermatitis such as atopic dermatitis, psoriasis or erythroderma and acute dermatitis such as rashes or other contact dermatitis, seborrheic dermatitis or solar dermatitis, and the use of a pharmaceutical agent, quasi drug or cosmetic incorporating the agent for sedating response to external stimulation in skin of the present invention results in less susceptibility to the occurrence of excessive reactions in the form of redness or itching that occur when the skin is subjected to various types of external stimulation, which in turn leads to treatment or prevention of the onset of inflammatory skin diseases. In the case of skin diseases such as atopic dermatitis in particular, since symptoms are exacerbated by scratching the affected site accompanying itchiness, reducing the likelihood of the occurrence of an excessive inflammatory reaction is useful for treatment.

The carboxymethyl-beta glucan used in the present invention is a beta glucan that has been modified to be water-soluble by carboxymethylation of an insoluble beta glucan. The carboxymethyl-beta glucan may be produced from a beta glucan derived from an arbitrary plant, fungus or bacteria or by synthesizing therefrom.

Naturally-occurring beta glucans may be produced by mushrooms such as *Agaricus blazei, Ganoderma lucidum* or *Schizophyllum commune*, or by yeast. The weight average molecular weight of carboxymethyl-beta glucan is, for example, 1,000 to 5,000,000 daltons corresponding to the source, and in the case of carboxymethyl-beta glucan obtained from yeast, the upper limit of the weight average molecular weight thereof is preferably 5,000,000 daltons, more preferably 3,000,000 daltons and even more preferably 2,000,000 daltons, while the lower limit is preferably 10,000 daltons, more preferably 100,000 daltons and even more preferably 500,0000 daltons. The carboxymethyl-beta glucan may also be in the form of an arbitrary salt, and may be in the form of, for example, a sodium salt, potassium salt, ammonium salt or triethanolamine salt. Although sodium carboxymethyl-beta glucan in the form of CM-Glucan (Mibelle Biochemistry) can be used as a commercially available carboxymethyl-beta glucan, commercially available carboxymethyl-beta glucans are not limited thereto. Although varying according to the drug form of the cosmetic or pharmaceutical in which it is incorporated, the incorporated amount thereof is, for example, 0.0001% by weight or more, preferably 0.0002% by weight or more and more preferably 0.002% by weight or more from the viewpoint of demonstrating adequate efficacy. On the other hand, the carboxymethyl-beta glucan is preferably used at 0.5% by weight or less, more preferably at 0.1% by weight or less and even more preferably at 0.01% by weight or less from the viewpoint of solubility.

The average number of moles added of the polyoxypropylene (POP) used in the polyoxyethylene (POE)/polyoxypropylene (POP) random copolymer dimethyl ether used in the present invention is preferably 2 to 50, the average number of moles of polyoxyethylene (POE) added is preferably 8 to 100, and the ratio of the average number of moles of polyoxyethylene (POE) added to the total number of moles of polyoxyethylene (POE) and polyoxypropylene (POP) added [POE/(POE+POP)] is preferably 0.5 or more. Here, POE and POP are the abbreviations for polyoxyethylene and polyoxypropylene, respectively, and hereinafter are abbreviated in the same manner. In addition, the molar ratio of polyoxyethylene to polyoxypropylene used in the polyoxyethylene (POE)/polyoxypropylene (POP) random copolymer dimethyl ether is within the range of 1:5 to 5:1, preferably within the range of 1:3 to 3:1 and more preferably within the range of 1:2 to 2:1 from the viewpoint of acquiring a polymer that demonstrates the desired action. For example, a polymer in which the ratio of POE:POP is 2:1 can be used. The polyoxyethylene (POE)/polyoxypropylene (POP) random copolymer dimethyl ether can be produced according to a known method (Patent Document 3). For example, after having added ethylene oxide and propylene oxide to a compound having a hydroxyl group by addition polymerization, the polyoxyethylene (POE)/polyoxypropylene (POP) random copolymer dimethyl ether is obtained by etherification of an alkyl halide in the presence of a basic catalyst. Although varying according to the drug form of the cosmetic or pharmaceutical agent in which it is incorporated, the incorporated amount thereof is, for example, 0.01% by weight or more, preferably 0.05% by weight or more and more preferably 0.1% by weight or more from the viewpoint of demonstrating adequate efficacy. On the other hand, the incorporated amount is preferably 3% by weight or less, more preferably 1% by weight or less and even more preferably 0.5% by weight or less from the viewpoint of solubility. In this connection, polyoxyethylene (POE)/polyoxypropylene (POP) random copolymer dimethyl ether is known to exert a moisturizing effect by itself, or in combination with another ingredient, whereas an effect relating to CD39 gene expression is not known for polyoxyethylene (POE)/polyoxypropylene (POP) random copolymer dimethyl ether.

The rosewater used in the present invention refers to an aqueous component having a fragrance that is obtained by steam distillation of petals of a plant belonging to the genus *Rosa*. Although the variety of rose used for the rosewater may be an arbitrary variety, examples of varieties that may be used include *Rosa damascena* Miller and *Rosa centifolia* L. Rosewater is obtained by subjecting rose petals to steam distillation at a high temperature and high pressure (e.g., 4 atm and 120° C.) followed by filtering the resulting aqueous layer component, after which the filtrate is used as is. The incorporated amount thereof is, for example, 0.01% (v/v) or more, preferably 0.5% (v/v) or more and more preferably 0.1% (v/v) or more from the viewpoint of demonstrating adequate efficacy. On the other hand, the incorporated amount is preferably 3% (v/v) or less, more preferably 1% (v/v) or less and even more preferably 0.5% (v/v) or less from the viewpoint of solubility.

The blending ratio of the carboxymethyl-beta glucan or salt thereof, polyoxyethylene (POE)/polyoxypropylene (POP) random copolymer dimethylether and rosewater used in the present invention is 1:1 to 100:1 to 100, preferably 1:1 to 20:1 to 20 and more preferably 1:10:10 based on a value of 1 for the incorporated amount of a 2% aqueous solution of the carboxymethyl-beta glucan or salt thereof.

The CD39 gene expression promoter, agent for sedating response to external stimulation and agent for sedating immune response in skin may respectively be incorporated in a cosmetic, pharmaceutical or quasi drug. These pharmaceutical agents may be administered orally, parenterally or transcutaneously. In the case of administering transcutaneously, the pharmaceutical agent can be in the form of an external skin preparation. There are no particular limitations on the external skin preparation provided it can be applied to skin, and examples of drug forms that can be applied include solutions, emulsions, solids, semi-solids, powders, separate water-oil two-layer preparations, separate water-oil-powder three-layer preparations, ointments, gels, aerosols, mousses, sticks and other arbitrary drug forms. In the case of formulating an external skin preparation, preparation bases as well as vehicles such as preservatives, emulsifiers or pH adjusters ordinarily used in external skin preparations may be used, and anti-inflammatory components such as steroids or antihistamines may also be added. In the case of incorporating in a cosmetic, the pharmaceutical agents of the present invention may be incorporated in cosmetics for the face or body, such as beauty washes, milky lotions, beauty lotions, creams, lotions, facial packs, essences or gels, in makeup cosmetics such as foundations, cosmetic bases or concealers, or in bath additives. Use of a cosmetic containing the components of the present invention makes it possible to maintain healthy skin less susceptible to the occurrence of redness, itchiness or rashes since the components of the present invention are able to alleviate or prevent inflammatory reactions.

The present invention also relates to a cosmetic application method, a method for sedating response to external stimulation, a method for maintaining healthy skin and a method for treating inflammation comprising administering the CD39 gene expression promoter, the agent for sedating response to external stimulation in skin, and the agent for sedating skin immune response of the present invention, namely three components consisting of carboxymethyl-beta glucan or salt thereof, polyoxyethylene (POE) 14/polyoxypropylene (POP) 7 random copolymer dimethyl ether and rosewater. In these methods, administration of the three components of the present invention may be carried out by using an external skin preparation or cosmetic incorporating all three components, or may be carried out by consecutively using external skin preparations or cosmetics incorporating individual components.

EXAMPLES

Example 1: CD39 Expression Promoting Effect of Each Component in Human Langerhans Cell-Like Cells THP-1 cells (American Type Culture Collection, VA, USA) were used as a substitute for human Langerhans cells. Approximately 200,000 THP-1 cells were cultured to confluence in RPMI1640 medium containing 10% FBS. Following culturing, stress hormone in the form of 10 nM dexamethasone was added followed by the respective addition of 0.1% polyoxyethylene (POE) 14/polyoxypropylene (POP) 7 random copolymer dimethyl ether (A), 0.01% of a 2% aqueous solution of sodium carboxymethyl-beta glucan (CM-Glucan, Mibelle Biochemistry) (B) and 0.1% rosewater (Bulgaria Rose Water, Toyotama International) (C). Moreover, a three-type mixture group (ABC) was added that incorporated one-third each of all three components. After culturing for 24 hours after addition, RNA was extracted using Isogen (Wako Pure Chemical Industries) followed by synthesis of cDNA using Superscript III and random primers (Invitrogen). RT-PCR was carried out with the Prism 7900HT (ABI) using SYBR Green (Invitrogen) and the primers indicated below.

```
CD39-Forward:
                                    (SEQ ID NO: 1)
GGAGAATGACACAGGCGTGGTGCATC CD39-Reverse:
                                    (SEQ ID NO: 2)
GTGGCTCCCAGGTAAACGGGTGTCT RPS9-Forward:
                                    (SEQ ID NO: 3)
TGCTGACGCTTGATGAGAAG RPS9-Reverse:
                                    (SEQ ID NO: 4)
CGCAGAGAGAAGTCGATGTG
```

During this RT-PCR, ribosomal protein S9 was used as normalization factor. The results are shown in FIG. 1. When stress hormone in the form of dexamethasone was added, expression of CD39 decreased in the Langerhans cell-like cells. In the case of respectively adding polyoxyethylene (POE) 14/polyoxypropylene (POP) 7 random copolymer dimethyl ether (Group A), sodium carboxymethyl-beta glucan (Group B) and rosewater (Group C), the decreased expression level of CD39 improved to a certain degree. On the other hand, in the case of adding the three-type mixture group (Group ABC) that incorporated one-third each of all three components, the decreased CD39 expression level recovered to nearly the same level as the expression level of a dexamethasone non-addition group, and a statistically significant improvement effect was demonstrated in comparison with the other test groups (groups A, B and C) ($p<0.01$, Scheffe's F test).

Example 2: Changes in CD39 Expression Levels Following

Application of Each Component in Test Subjects

Figure 2:
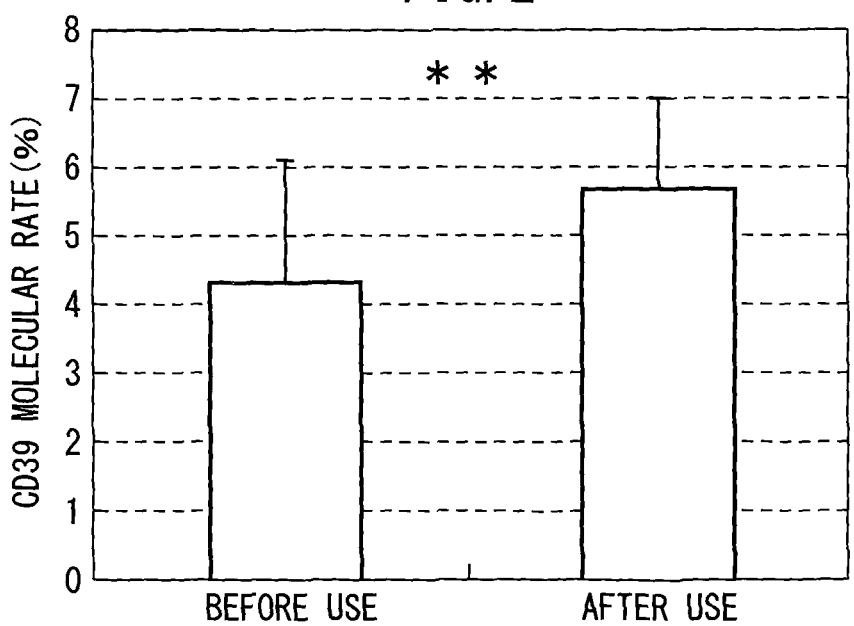
FIG. 2 indicates changes in the amount of CD39 molecules during application of the cosmetic shown in Table 1 containing sodium carboxymethyl-beta glucan, polyoxyethylene (POE) 14/polyoxypropylene (POP) 7 random copolymer dimethyl ether and rosewater.

A cosmetic containing 0.1% polyoxyethylene (POE) 14/polyoxypropylene (POP) 7 random copolymer dimethyl ether, 0.01% of a 2% aqueous solution of sodium carboxymethyl-beta glucan (CM-Glucan, Mibelle Biochemistry) and 0.1% rosewater (Bulgaria Rose Water, Toyotama International) (refer to Table 1 for the detailed composition) was used in an application test. The cosmetic described in Table 1 was applied twice a day for 6 weeks to 10 healthy male subjects age 20 to 30 and 12 healthy male subjects age 49 to 58. Samples of the epidermis were collected by a physician using the suction blistering method. The suction blistering method was carried out in accordance with Non-Patent Document 4 before and after continuous application, and samples of the epidermis were collected by contacting a syringe connected to the end of a vacuum pump with the skin, suctioning for 30 minutes to 60 minutes, and cutting away the epidermis where the blister had formed. The collected epidermis was washed with phosphate-buffered saline (PBS), fixed with acetone and blocked with 10% goat serum, followed by immunofluorescent staining with anti-CD39 antibody (ab97552, Abcam) and Alexa Fluor 488-labeled goat anti-mouse antibody (Alexa Fluor 488, Molecular Probes, A11001). Cross-sectional images were obtained using a laser scanning confocal microscope (Pascal, Zeiss), and the resulting images were quantitatively analyzed for the proportion of positive sites using image analysis software (IP Labo 4.0, Solution System). The results are shown in FIG. 2. As a result of applying a cosmetic comprising a mixture of polyoxyethylene (POE) 14/polyoxypropylene (POP) 7 random copolymer dimethyl ether, 2% aqueous solution of sodium carboxymethyl-beta glucan and rosewater to the forearm for 6 weeks, CD39 molecules present in the epidermis increased significantly (FIG. 2).

TABLE 1

| Raw Materials | Incorporated Amount (%) |
|---|---|
| Ethanol | 5 |
| Glycerin | 1 |
| 1,3-butyleneglycol | 5 |
| Acrylic acid-alkyl methacrylic acid copolymer | 0.1 |
| Carboxyvinyl polymer | 0.1 |
| Potassium hydroxide | 0.1 |
| Glyceryl tri-2-ethylene hexanoate | 4 |
| dl-α-tocopherol acetate | 0.1 |
| Polyoxyethylene(14)/polyoxypropylene(7) dimethyl ether | 0.1 |
| Sodium carboxymethyl-beta glucan (2% aqueous solution) | 0.01 |
| Rosewater | 0.1 |
| Fragrance | 0.1 |
| Purified water | 84.29 |

FORMULATION EXAMPLES

TABLE 2

| Raw Materials | Incorporated Amount (%) |
|---|---|
| Dimethylpolysiloxane | 1 |
| Glycerin | 3 |
| 1,3-butyleneglycol | 6 |
| Polyethylene glycol 1500 | 4 |
| Squalane | 5 |
| Stearyl alcohol | 3 |
| Carboxyvinyl polymer | 0.2 |
| Alkyl Acrylate/Methacrylate copolymer | 0.1 |
| Polyoxyethylene(14)/polyoxypropylene(7) dimethyl ether | 0.5 |
| Sodium carboxymethyl-beta glucan (2% aqueous solution) | 0.05 |
| Rosewater | 0.2 |
| Preservative agent | As suitable |
| Fragrance | As suitable |
| Purified water | Balance |

TABLE 3

| Raw Materials | Incorporated Amount (%) |
|---|---|
| Dimethylpolysiloxane | 1 |
| Ethanol | 3 |
| Behenyl alcohol | 0.3 |
| Glycerin | 5 |
| Dipropylene glycol | 5 |
| Erythritol | 1 |
| Polyethylene glycol 4000 | 1 |
| Squalane | 0.4 |
| Cetyl 2-ethylhexanoate | 0.1 |
| Sodium N-stearoyl-L-glutamate | 0.2 |
| Magnesium chloride | 0.1 |
| Arginine chloride | 0.1 |
| Trisodium edetate | 0.1 |
| Polyoxyethylene(14)/polyoxypropylene(7) dimethyl ether | 1 |
| Sodium carboxymethyl-beta glucan (2% aqueous solution) | 0.1 |
| Rosewater | 0.01 |
| Preservative agent | As suitable |
| Fragrance | As suitable |
| Purified water | Balance |

The invention claimed is:

1. A topical cosmetic CD39 gene expression promoter composition consisting essentially of effective amounts of carboxymethyl-beta glucan or a salt thereof, polyoxyethylene (POE)/polyoxypropylene (POP) random copolymer dimethyl ether and rosewater.

2. The topical cosmetic CD39 gene expression promoter composition of claim 1, wherein the components are in a ratio of 1:1 to 100:1 to 100 of carboxymethyl-beta glucan or a salt thereof: polyoxyethylene (POE)/polyoxypropylene (POP) random copolymer dimethyl ether:rosewater.

3. The topical cosmetic CD39 gene expression promoter composition of claim 1, wherein the effective amounts consist of 0.0001-0.5 wt. % of carboxymethyl-beta glucan or a salt thereof, 0.01-3 wt. % of polyoxyethylene (POE)/polyoxypropylene (POP) random copolymer dimethyl ether, and 0.01-3% v/v rosewater.

* * * * *

SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ggagaatgac acaggcgtgg tgcatc                    26

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gtggctccca ggtaaacggg tgtct                     25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
tgctgacgct tgatgagaag                           20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
cgcagagaga agtcgatgtg                           20